United States Patent [19]

Seres et al.

[11] 4,252,114
[45] Feb. 24, 1981

[54] BREATHING BAG ASSEMBLY

[75] Inventors: Robert J. Seres, Allison Park; Frank J. Lotito, Pittsburgh, both of Pa.

[73] Assignee: Mine Safety Appliances Company, Pittsburgh, Pa.

[21] Appl. No.: 53,229

[22] Filed: Jun. 29, 1979

[51] Int. Cl.$^3$ .............................................. A62B 7/00
[52] U.S. Cl. ............................ 128/205.16; 128/205.24
[58] Field of Search .................. 128/205.16, 205.15, 128/205.13, 205.17, 205.22, 205.12, 728, 203.28, 204.28; 251/337; 92/94, 95

[56] References Cited
FOREIGN PATENT DOCUMENTS

| | | | |
|---|---|---|---|
| 581026 | 9/1924 | France | 128/205.12 |
| 591530 | 8/1947 | United Kingdom | 128/205.16 |
| 1039739 | 8/1966 | United Kingdom | 128/205.13 |

*Primary Examiner*—Henry J. Recla
*Attorney, Agent, or Firm*—Brown, Flick & Peckham

[57] ABSTRACT

A breathing bag inside a rigid case has an inlet and an outlet connected with openings in the case. There is a pressure plate inside the case between one side of it and the bag, the plate being movable toward and away from the opposite side of the case. Also inside the case and disposed between it and the plate is a plurality of lever arms, each of which has a free end engaging the plate, with the opposite end of the arm rigidly connected to a torsion bar spring extending laterally away from the arm to a point where it is rigidly connected to the case. While the bag is deflated, the bars hold the lever arms inclined to the plate so that the arms will resist movement of the plate as the bag is inflated and thereby maintain a positive air pressure in the bag.

8 Claims, 5 Drawing Figures

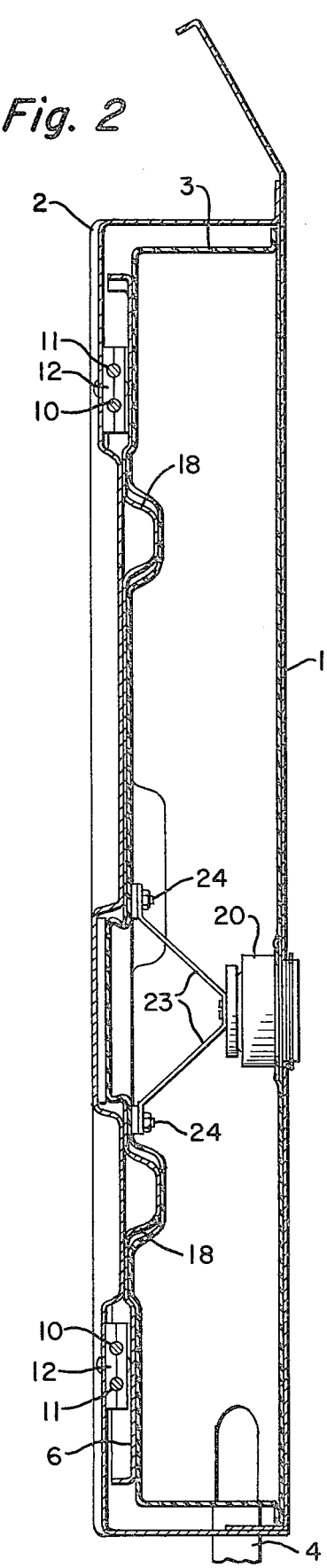
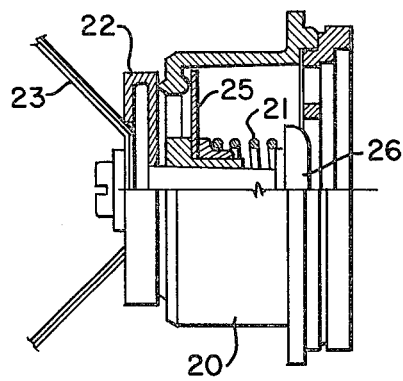
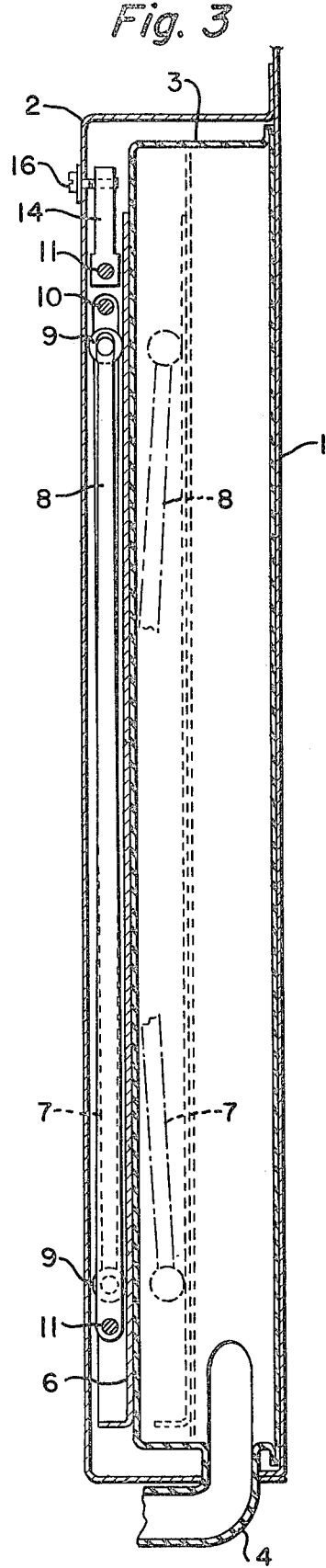
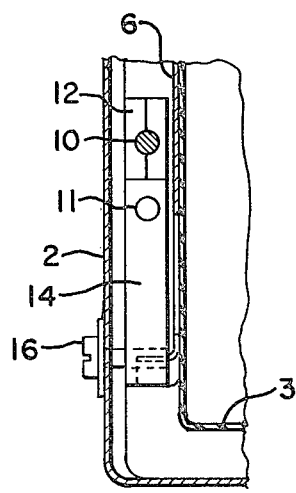

BREATHING BAG ASSEMBLY

In closed-circuit breathing apparatus, it is desirable to maintain a positive pressure in the breathing bag so that any leakage in the system will be outward and not into it. One way of doing this is to exert spring pressure against the bag so that it will resist inflation and thereby cause a build up of pressure in the bag. Various spring arrangements for this purpose have been proposed, such as shown in U.S. Pat. Nos. 1,533,172 and 1,679,115 and French Pat. No. 1,336,301, but it is an object of this invention to improve upon the prior art and to provide for adjusting the spring pressure against the breathing bag.

The preferred embodiment of the invention is illustrated in the accompanying drawings, in which FIG. 1 is an elevation, with the case cover partly broken;

FIGS. 2 and 3 are vertical cross sections taken on the lines II—II and III—III, respectively, of FIG. 1;

FIG. 4 is a fragmentary cross section taken on the line IV—IV of FIG. 1; and

FIG. 5 is an enlarged combination elevation and cross section of the pressure relief valve.

Figure 1:
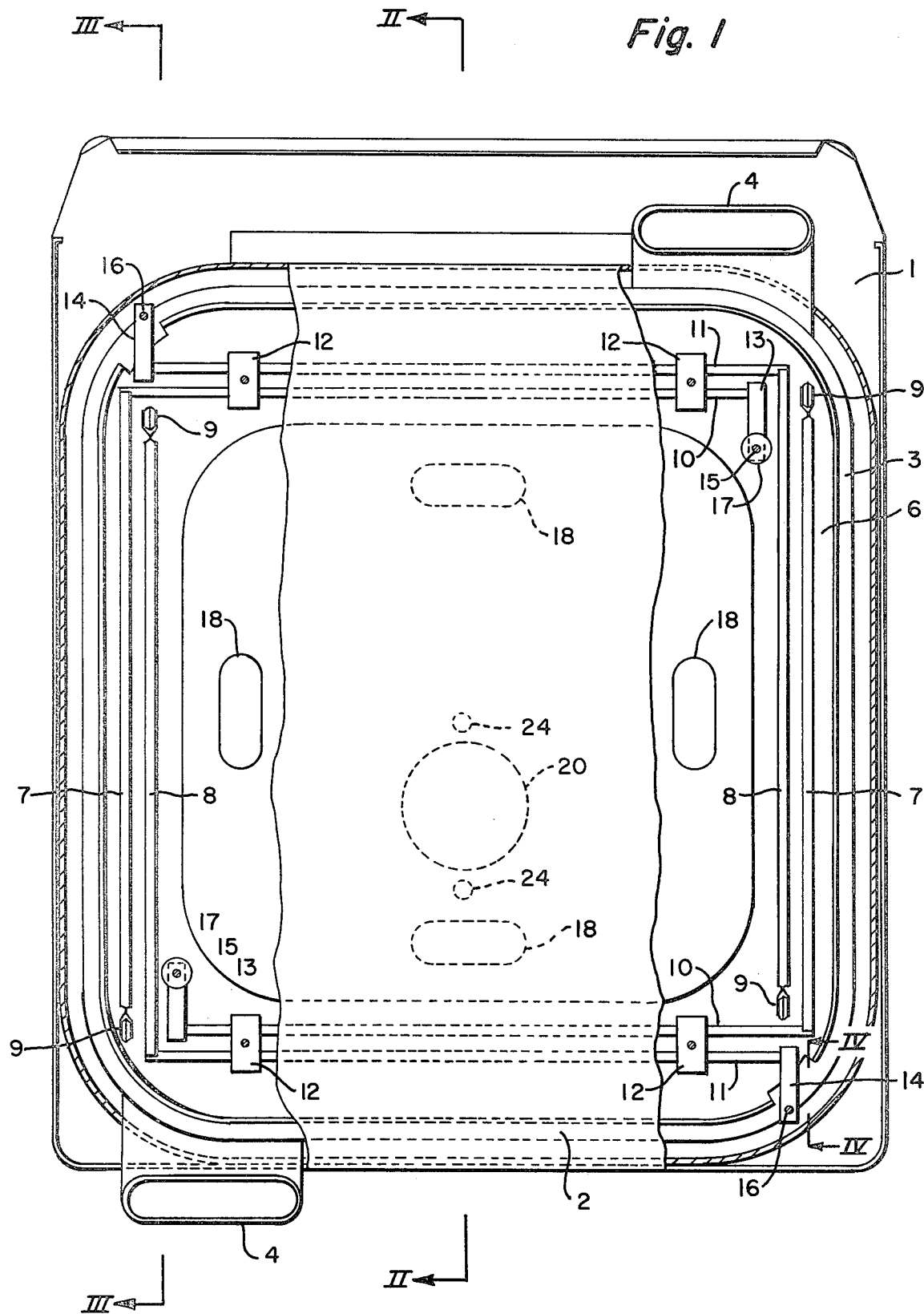

Referring to the drawings, a relatively thin, rigid, rectangular case made of any suitable material, such as metal, is formed from a back plate 1, to which a cover 2 is attached. Disposed inside of this case is a flexible breathing bag 3 that is provided with an inlet opening and an outlet opening. Preferably, the bag openings are disposed beside corresponding openings in the corners of the case. Flexible tubes 4 extend from the bag openings through the case openings and have outer ends suitable for connection into a closed-circuit breathing system in a well known manner.

Between one side of the case and the adjacent side of the bag there is a floating pressure plate 6 that covers most of that side of the bag. The plate, which is movable toward and away from the opposite side of the bag, can be attached to the bag in any suitable manner, such as by an adhesive.

Between the pressure plate and the opposing side of the case, which is the cover 2, there are resilient means that urge the pressure plate away from that side of the case and thereby resist its movement toward the cover during expansion of the bag by exhalation into it. The resilient means include parallel lever arms 7 and 8, one end of each of which is forked and provided with a roller 9 that engages the pressure plate. The other end of each arm is rigidly connected to one end of a torsion bar spring that extends laterally away from the arm and across the case. Thus, arm 7 is connected to torsion bar 10 and arm 8 is connected to torsion arm 11. Near the ends of the torsion bars they are rotatably mounted in bearing blocks 12 attached to the side of the case. Rigidly mounted on the end of bar 10 opposite to arm 7 is a laterally extending lug 13 that extends inwardly away from the adjacent bar 11. With the lugs substantially parallel to the adjacent side of the case, the unstressed position of the lever arms is inclined to that side of the case. FIG. 3 shows in dotted lines the arms only partially stressed. The outer ends of the lugs are provided with openings in which are threaded screws 15 and 16 that are rotatably mounted in the cover of the case. These screws prevent the lugs from turning and thereby prevent the adjoining ends of the torsion bars from turning, whereby the lug ends of the bars are rigidly mounted in the case.

Preferably, four lever arms are used, arranged in two pairs spaced widely apart beside marginal areas of the pressure plate. The roller on one arm 7 in each pair engages the plate near one corner, and the roller on the other arm 8 in the same pair engages the plate near another corner, so the two lever arms extend in opposite directions from their rollers. With four lever arms, of course there are four torsion bars, likewise arranged in pairs. The screw 16 in lug 14 prevents the lug from being swung away from the cover when lever arm 8 is swung outwardly by the pressure plate during expansion of the breathing bag, so by adjusting the screw the spring tension of the torsion bar can be increased or decreased. Since the other lug 13 tends to be swung toward the adjacent side of the case as arm 7 is swung toward that side, a nut 17 is welded to the cover so that adjusting screw 15 can force the lug away from the case to increase the tension on torsion bar 10.

When the breathing bag is not being used, the torsion bars cause the lever arms to press the pressure plate toward the opposite side of the case. At such time, the lever arms in each pair are inclined to the plate and cross each other as shown in dotted lines in FIG. 3. The pressure plate is provided with bosses 18 that prevent the bag from being collapsed completely, whereby there always is a reserve supply of air in the bag. When the bag is in use, exhalation into it will overcome the resistance of the torsion bars and thereby inflate the bag, but of course the torsion bars and lever arms resist the outward movement of the pressure plate, with the result that the air pressure in the bag is greater than atmospheric.

To prevent overpressurizing of the bag, it is provided with a relief valve 20 in the side opposite the pressure plate. The valve extends through the adjoining side of the case and is fastened to it. Normally, as shown in FIG. 5, the valve is held closed by a spring 21, but just before the bag becomes fully expanded, further exhalation into it will cause the movable valve member 22 to be pulled off its seat by means of flexible tapes 23 connected with the side of the bag engaged by the pressure plate. The ends of these tapes may be connected by bolts 24 to the pressure plate. Excess pressure in the bag will force valve flap 25 off its seat and allow air to escape from the bag. The bag can be deflated manually by pressing on a button 26 connected to valve member 22.

According to the provisions of the patent statutes, we have explained the principle of our invention and have illustrated and described what we now consider to represent its best embodiment. However, we desire to have it understood that, within the scope of the appended claims, the invention may be practiced otherwise than as specifically illustrated and described.

We claim:

1. A breathing bag assembly for closed-circuit breathing apparatus, comprising a rigid case provided with a pair of openings, a breathing bag inside the case provided with inlet and outlet openings connected with said case openings, a pressure plate inside the case between one side of the case and the bag and movable toward and away from the opposite side of the case, a plurality of lever arms inside the case disposed between its said one side and plate, one end of each arm engaging the plate, a separate torsion bar spring for each lever arm rigidly connected at one end to the opposite end of the arm and extending laterally away from it, and means rigidly connecting the opposite end of each bar to the case, the bars serving as pivotal mountings for said opposite ends of the arms to permit the plate-engaging ends of the arms to be swung toward and away from said one side of the case, the bars holding the lever arms inclined to said pressure plate while the bag is deflated with the plate adjacent said opposite side of the case, whereby the lever arms will resist movement of the plate toward said one side of the case as the bag is inflated.

2. A breathing bag assembly according to claim 1, including a bearing block receiving each torsion bar adjacent its lever arm and rigidly secured to said case.

3. A breathing bag assembly according to claim 1, including means limiting the distance the pressure plate can be moved toward said opposite side of said case, whereby to prevent complete closing of the bag.

4. A breathing bag assembly according to claim 1, in which there are two laterally spaced parallel pairs of said lever arms, two laterally spaced parallel pairs of said torsion bars perpendicular to the arms, and the lever arms in each pair extend in opposite directions from their free ends and cross each other while the bag is deflated so that the free end of each arm in each pair is adjacent the torsion bar connected to the other arm in the same pair.

5. A breathing bag assembly according to claim 1, including means for adjusting the pressure that said torsion bars exert on the lever arms.

6. A breathing bag assembly according to claim 1, in which said connecting means include a lug rigidly attached to said opposite end of each torsion bar and projecting laterally therefrom, and means connecting the outer end of each lug to said case.

7. A breathing bag assembly according to claim 6, in which said last-mentioned connecting means is a screw rotatably mounted in said one side of the case and threaded in the adjoining lug, whereby said opposite end of the torsion bar attached to the lug can be turned by turning the screw to adjust the pressure that the bar will exert on its lever arm.

8. A breathing bag assembly according to claim 1, including a pressure relief valve mounted in the side of said bag opposite said pressure plate, means attaching said valve to said opposite side of the case, the valve includng a spring-pressed valve member normally closing the valve, and means connecting said valve and plate for opening the valve whenever the bag starts to be inflated more than a predetermined amount, said means connecting the valve and pressure plate being a flexible tension member connected to said valve member for pulling it from its seat when the plate moves more than a predetermined distance away from said opposite side of the case.

* * * * *